(12) United States Patent
Tarletsky et al.

(10) Patent No.: US 7,407,666 B2
(45) Date of Patent: *Aug. 5, 2008

(54) LINEAR SILICONE RESINS IN PERSONAL CARE APPLICATIONS

(75) Inventors: Christopher Tarletsky, Stewartsville, NJ (US); Adam Perle, Saddle River, NJ (US); Anthony J. O'Lenick, Jr., Dacula, GA (US)

(73) Assignees: Siltech LLC, Dacnia, GA (US); Jeen International Corp, Fairfield, NJ (US)

( * ) Notice: Subject to any disclaimer, the term of this patent is extended or adjusted under 35 U.S.C. 154(b) by 104 days.

This patent is subject to a terminal disclaimer.

(21) Appl. No.: 11/359,939

(22) Filed: Feb. 23, 2006

(65) Prior Publication Data

US 2007/0196309 A1    Aug. 23, 2007

(51) Int. Cl.
*A61K 8/02* (2006.01)
*A61K 8/04* (2006.01)
*A61K 31/695* (2006.01)

(52) U.S. Cl. .......................... 424/401; 424/600; 514/63; 514/937

(58) Field of Classification Search ................ 424/401, 424/600; 514/63, 937
See application file for complete search history.

(56) References Cited

U.S. PATENT DOCUMENTS 6,139,823 A * 10/2000 Drechsler et al. ............. 424/64
2007/0010408 A1 * 1/2007 Uehara ........................ 510/119

* cited by examiner

*Primary Examiner*—Johann R. Richter
*Assistant Examiner*—Konata M. George

(57) ABSTRACT

The present invention relates to the use in personal care products of a series of novel silicone polymers (referred to as linear silicone resin) that by are made by the hydrosilylation reaction of a terminal vinyl silicone and a terminal silanic hydrogen polymer. The properties make the compounds very useful in a variety of personal care applications including personal care.

16 Claims, No Drawings

LINEAR SILICONE RESINS IN PERSONAL CARE APPLICATIONS

FIELD OF THE INVENTION

The present invention relates to the use in personal care products of a series of novel silicone polymers (referred to as linear silicone resin) that by are made by the hydrosilylation reaction of a terminal vinyl silicone and a terminal silanic hydrogen polymer. The properties make the compounds very useful in a variety of personal care applications including personal care. Linear silicone reins and solvent blends offer a unique spread and texture for topical applications to skin hair resulting in matte, moderate gloss and high gloss properties for oil in water, water in oil. In addition, these linear silicone resin blends also offer a unique spread and texture for cosmetic applications of face, eye and lips also resulting in Matte, gloss and high gloss properties this is due in part to the ability to alter the refractive index range for the linear silicone resins alone and in mixture with solvents. The invention is in the field of compositions for application to keratinous surfaces such as eyebrows, eyelashes, eyelids, facial or body skin, lips, or hair for the purpose of coloring, conditioning, or beautifying the keratinous surface.

BACKGROUND OF THE INVENTION

Manufacturers of cosmetic products are on an eternal quest to formulate cosmetic compositions that provide better films on keratinous surfaces. The ideal cosmetic film lasts until the consumer wants to remove it by washing with water or using remover compositions. At the same time the film provides a very natural, aesthetic appearance on the keratinous surface without looking fake or "made up". A suitable cosmetic film should permit the underlying keratinous surface to breathe, retain moisture, and exhibit a superficially attractive appearance that is not too artificial in appearance.

Most often, polymers are incorporated into cosmetic compositions to form the cosmetic film. Generally, such polymers contain many repeating units, or monomers, that give the polymer substantive, film forming properties. Such polymers may be natural or synthetic. Natural polymers such as cellulosics, gums, and resins, have been used as film formers in cosmetics for many years. In more recent years, as polymer chemistry has advanced, polymer manufacturers have been able to manufacture a wide variety of synthetic polymers for use in cosmetics. In general, synthetic polymers fall into one of two classes: silicone polymers (based upon silicon and oxygen), or organic polymers comprised of repeating organic moieties, for example, polymers obtained by polymerizing ethylenically unsaturated monomers such as acrylates or alkylenes, optionally with organic moieties such as amides, urethanes, and the like. Certain synthetic polymers that contain both siloxane monomers and organic moieties are also known.

While synthetic polymers comprised of organic moieties such as ethylenically unsaturated monomers are excellent film formers, they sometimes do not exhibit optimal properties on keratinous surfaces such as skin. Skin is a very dynamic substrate that is in constant movement so cosmetic films that are affixed to skin or lips must exhibit some degree of plasticity. Synthetic organic polymers do not always exhibit the necessary plasticity, and will sometimes crack on dynamic keratinous surfaces such as skin. For this reason, synthetic organic polymers are not as widely used in cosmetic compositions that are applied to skin.

On the other hand, silicone polymers are excellent film formers and have been used to form cosmetic films in many successful commercial products. While silicones provide excellent wear and adhesion in general, organic synthetic polymers often provide desired surface properties that are lacking in silicones. It has been found that a certain silicone polymer, referred to as linear silicone resin, when used in cosmetic compositions, provides excellent substantivity to the composition, promotes formation of a suitable cosmetic film, and provides a light, pleasant feel to the composition.

The term silicone resin has been applied both to and misapplied to a variety of materials over time. Silicone resins as used herein refer to a series of products which include at least two silicone backbones that are joined by a "crosslinking group". The number of crosslinking groups that are present as a percentage of the total molecular weight will determine the properties of the resulting polymer. Quite to the contrary, our compounds, although the reaction of linear SiH and linear vinyl siloxanes, form elastomeric films when the solvent is removed. We have no crosslinking groups and consequently are quite surprised that the compounds are film formers. While not wanting to be bound by any one theory, we believe that as the polymers grow, "backbiting" occurs forming cyclic structures. A number of materials cyclize forming an interlocked system of cyclic compounds making a film as the solvent evaporates.

Our compounds surprisingly and in an unexpected manner have no crosslinking groups, but form films. As previously stated we believe this is because of interlocking of the cyclic structures. The size of the cyclic is controlled by the choice of raw materials. As will become clear, there are two competing reactions, chain growth and cyclization.

The literature contains many patents that deal with silicone resins. Many patents deal with improvements of the resins. However, there are only a number of classes of resin compounds differing in the nature of the crosslinker. One class is the so called "Q resins".

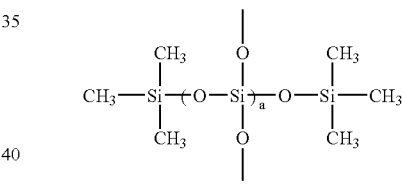

The oxygen that needs another bond connects to another polymer as shown:

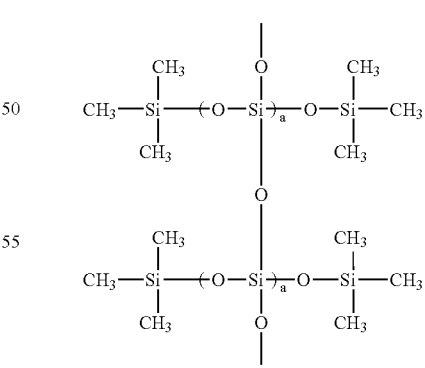

The crosslinking group is —O—. This type of resin is disclosed in U.S. Pat. No. 6,139,823, incorporated herein by reference. This type of material has a tetrafunctional "Q" group in which the Si has four oxygen atoms attached. This type of resin is very powdery and is rarely used without a plasticizer. This class of compounds can also dry the skin.

The next class of resin contain alkyl connecting groups.

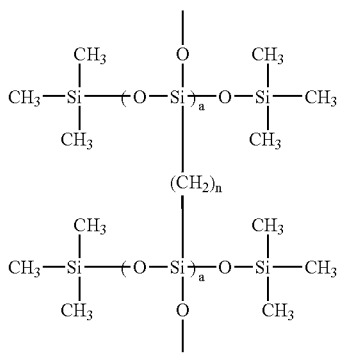

In the case where n=1 a multi functional SiH fluid is hydrosilated with a multifunctional vinyl siloxane. As n is increased the reactant is an alpha omega divinyl compound reacted with a multifunctional SiH fluid.

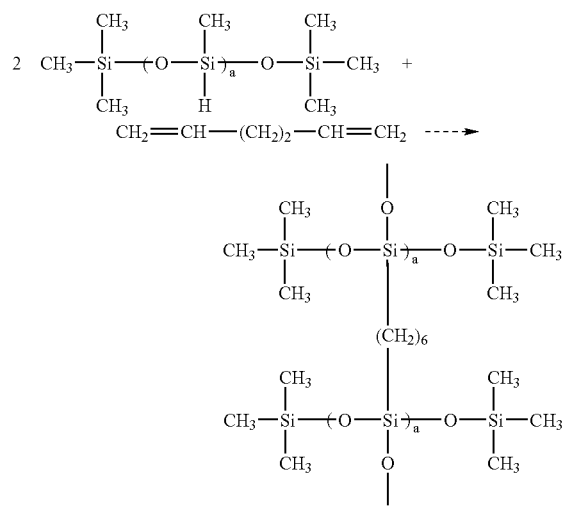

The SiH polymer is crosslinked with the organic divinyl molecule by reacting the vinyl with the SiH groups using the hydrosilation reaction. The reaction is generally run in solvent such as cyclomethicone (D4 or D5 or hexamethyl disiloxane) or in volatile organic like isododecane. A catalyst, generally a platinum based one, is used to effect the reaction. Chloroplatinic acid or platinum divinyl (commonly referred to as Karstedt) catalyst are preferred. The resulting material is a viscous liquid that when the solvent evaporates provides a film. The commonality here is that until the compounds of the present invention it was felt that all film forming resins had to be crosslinked. Our products refute that long held position.

U.S. patent application 20040180020 entitled Cosmetic compositions published Sep. 16, 2004 to Manelski, Jean Marie; et al., incorporated herein by reference discloses Compositions of the invention containing at least one cyclized dimethicone. The term "cyclized dimethicone" means an organosiloxane comprised of repeating —[Si—O$_2$]—, or "D" units, which form one or more cyclized portions in the final polymer. The cyclized portions, or rings, are formed by cross linking certain portions along the organosiloxane chain to form rings that may be structurally aligned along the polymeric chain. The claimed polymers are known compounds and are stated to have the INCI name dimethicone crosspolymer-3) and isododecane; or JEECHEM HPIB which is a mixture of cyclized dimethicone (dimethicone crosspolymer-3) and hydrogenated polyisobutene and cyclomethicone. Unlike the compounds of the present invention these polymers are cross linked internally with a carbon based cross linking agent. The materials are made by the reaction of an internal silanic hydrogen compound and a divinyl organic. Typical of the reaction is below:

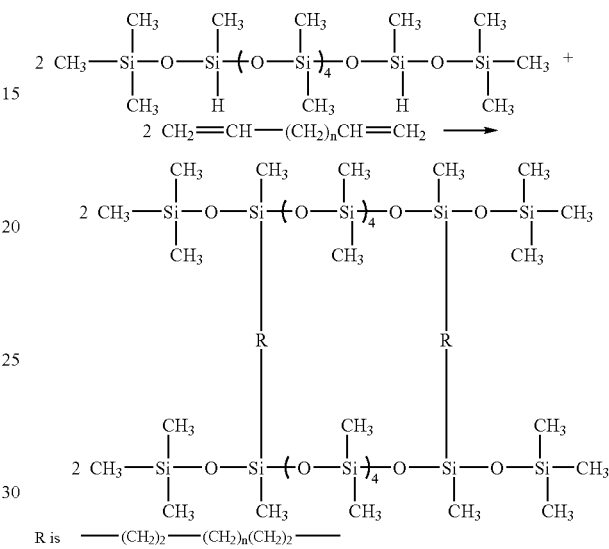

The above compounds are referred to as cyclized dimethicone by the referenced patent application. The cyclization results by the "boxing out" of the silanic hydrogen moiety with the organo functionality introduced with the alpha omega divinyl compound. It will be clearly noted that the compounds so described are not truly dimethicone since there are sections of the molecule that are organofunctional. Also please additionally note the branching pattern is internal, that is the organic functional ring can only occur using non-terminal silanic hydrogen compounds.

The compositions of the present invention contain neither organic cross linkers derived from alpha omega divinyl compounds nor are they internally branched.

In theory silicone fluids with no crosslinking groups can freely rotate and consequently are free flowing oily liquids. If a few crosslinking groups are introduced, the ability to rotate is slightly restricted and the oily material becomes "rubbery". The rubbery material should be referred to as an elastomer. The properties are morel like a rubber band than plastic. As the percentage of crosslinking increases the molecule becomes more rigid. These class of compounds are resins.

Our compounds surprisingly and in an unexpected manner have no crosslinking groups, but form films. As previously stated we believe this is because of interlocking of the cyclic structures. The size of the cyclic is controlled by the choice of raw materials. As will become clear, there are two competing reactions, chain growth and cyclization. We have surprisingly found that this pattern results in properties heretofore unknown in resin technology. None of the compounds of the prior art anticipate or make obvious the film forming compounds of the present invention.

OBJECT OF THE INVENTION

It is an object of the invention to provide a cosmetic composition with excellent wear and adhesion to keratinous surfaces.

It is another object of the invention to provide a cosmetic composition that provides a composition that exhibits excellent film forming properties.

It is another object of the invention to provide a mascara that lengthens, colors, and curls lashes, and exhibits long wearing properties.

It is another object of the invention to provide a lipstick composition that is long wearing and provides a glossy finish.

It is another object of the invention to provide cosmetic compositions for application to keratinous surfaces that look natural, provide a rich color, and exhibit reduced smudging.

Another object of the invention is to provide commercially acceptable, stable, cosmetic products for making up keratinous surfaces.

It is the object of the present invention to apply to the hair and skin a series of silicone film forming polymers that have no crosslinking groups. The compounds are made by reacting linear divinyl silicone and linear silanic hydrogen compounds.

Another object of the present invention is to provide a series of products suitable for formulation into personal care products including but not limited to lipsticks, mascara, hair and skin care compositions.

Other objects of the invention will become clear as one reads the specification attached hereto.

All charges given herein are % by weight, all temperatures are ° C., all patents and publications referred to herein are incorporated herein by reference in their entirety as appropriate.

SUMMARY OF THE INVENTION

Disclosed herein is a process for treating hair and skin which comprises contacting the hair and skin with an effective film forming concentration of a specific resin. These films are used in cosmetic makeup or care composition for the skin, including the scalp, of both the human face and body, the lips or the epidermal derivatives of humans, such as hair, eyelashes, eyebrows and nails, which comprises, in a cosmetically acceptable medium, at least one specific polyester.

The present invention relates to a process for providing a film to the hair and skin which comprises contacting the hair and skin with an effective film forming concentration of a silicone resins that provide films that are cosmetically acceptable and are free of crosslinking groups.

The compositions of the present invention containing between 0.1 and 50% by weight of the compounds made by reacting specific alpha omega di-vinyl siloxane compounds with a specific alpha omega di-silanic hydrogen containing silicone compounds. The reaction is conducted in a suitable solvent selected from the group consisting of cyclomethicone (D-4 and D-5 and mixtures thereof) and isoalkanes (isododecane).

The invention comprises a cosmetic composition comprising specific silicone resin solvated or dispersed in a cosmetically acceptable carrier.

The invention further comprises a cosmetic composition comprising at least one linear silicone resin and at least one non-silicone polymer in a cosmetically acceptable carrier.

The invention further comprises a cosmetic composition comprising at least one linear silicone resin in combination with at least one silicone polymer in a cosmetically acceptable carrier.

The invention further comprises a cosmetic composition comprising at least one linear silicone resin in combination with at least one polymer comprised of silicone monomers and organic monomers.

The invention further comprises a cosmetic composition comprising at least one linear silicone resin in a cosmetically acceptable water and oil emulsion carrier.

The invention further comprises a cosmetic composition comprising at least one linear silicone resin in an anhydrous cosmetically acceptable carrier.

DETAILED DESCRIPTION

The cosmetically acceptable carrier may generally be anhydrous, or in the form of a water-in-oil or oil-in-water emulsion, the latter containing a water phase and an oil phase.

I. The Linear Silicone resin

Resins of the present invention are a class of silicone compounds which are prepared by the reaction of a di-vinyl silicone compound reacted with a terminal divinyl silanic hydrogen containing compound.

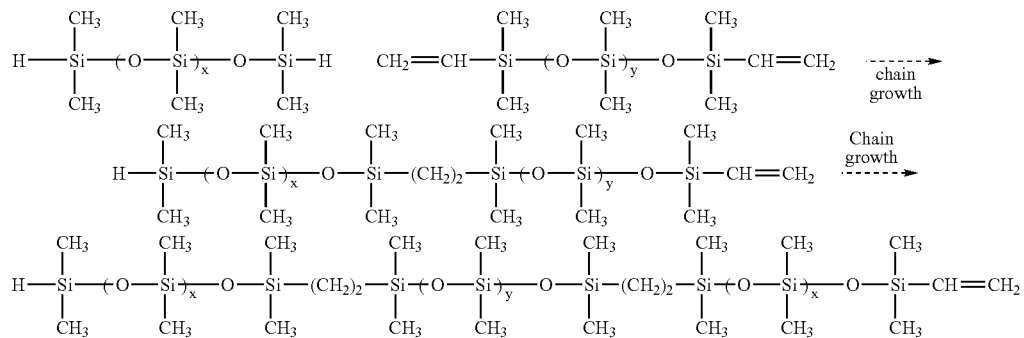

The terminal vinyl and terminal SiH on the same polymer chain eventually react with each other forming the chain. The length of the chain at which this backbiting occurs is solvent dependant. Larger molecular weight chains appear to form in hydrocarbon rather than in cyclomethicone solvents.

The resulting material is:

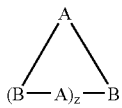

wherein;
A is

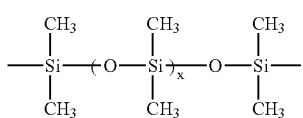

B is:

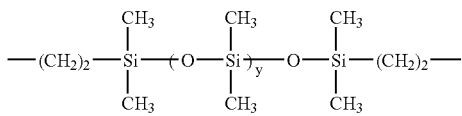

x is an integer ranging from 0 to 5000;
y is an integer ranging from 0 to 5000;
z is integer ranging from 2 to 2000.

Elastomers of the present invention are a class of silicone compounds which are prepared by the reaction of a di-vinyl silicone conforming to the following structure:

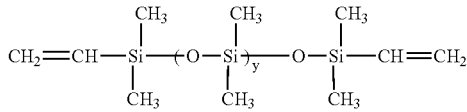

with a silanic hydrogen polymer conforming to the following structure:

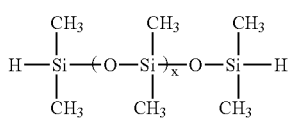

in the presence of a suitable hydrosilylation catalyst to produce a polymer conforming to the following structure:

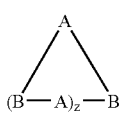

wherein;
A is

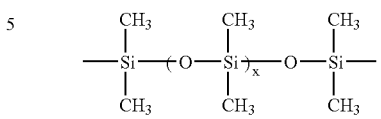

B is:

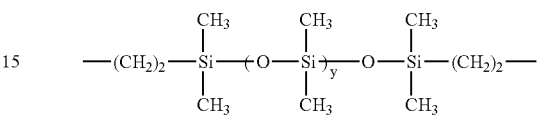

$x$ is an integer ranging from 0 to 5000;
$y$ is an integer ranging from 0 to 5000;
$z$ is integer ranging from 2 to 2000.

The reactions are typically carried out in a solvent, either volatile silicone (cyclomethicone (D4 or D5 or mixtures thereof) or hydrocarbon solvent like isododecane. A suitable hydrosilylation catalyst like chloroplatinic acid or Karstedt catalyst are used.

The value of "z" determines if the product is resinous or elastomeric. Elastomeric materials are compounds that are "rubbery" producing films that are rubber band like. Resins in contrast are not rubbery, but are hard and brittle.

One type of cosmetic composition of the present invention is color cosmetics designed to provide improved transfer resistance comprising:

a) 1-70% of a volatile solvent having a viscosity of about 0.5 to 20 centipoise at 25° C. and selected from the group consisting of volatile silicones, C. 8-20 isoparaffins, and mixtures thereof,
b) 0.1-5% of the silicone resins of the present invention
c) 10-45% of a wax selected from the group consisting of synthetic wax, ceresin, paraffin, ozokerite, illipe butter, beeswax, carnauba, microcrystalline, lanolin, candelilla, cocoa butter, shellac wax, spermaceti, bran wax, capok wax, sugar cane wax, montan wax, whale wax, bayberry wax, and mixtures thereof,
d) 5-50% of a powder component which is a dry, particulate matter comprised of pigments and powders having a particle size of 0.02 to 50 microns wherein the pigment to powder weight ratio ranges from 1:20 to 20:1, and
e) 1-30% oil, Preferred Embodiments In a preferred embodiment x is an integer ranging from 5 to 200.

In a preferred embodiment y is an integer ranging from 5 to 20.

In a preferred embodiment the catalyst is chloroplatinic acid.

In another preferred embodiment the preferred catalyst is Karstedt catalyst.

In a preferred embodiment there is an excess of silanic hydrogen compound relative to vinyl compound present in the reaction mixture.

In a preferred embodiment there is a 10% by weight excess of silanic hydrogen compound relative to vinyl compound present in the reaction mixture.

In a preferred embodiment x is an integer ranging from 10 to 100.

In a preferred embodiment y is an integer ranging from 10 to 100.

In a preferred embodiment x is an integer ranging from 10 to 50.

In a preferred embodiment y is an integer ranging from 10 to 50.

In a preferred embodiment the film forming resin is applied to the skin.

In a preferred embodiment the film forming resin is applied to the hair.

In a preferred embodiment the film forming resin is in a lipstick.

In a preferred embodiment the film forming resin is in a mascara.

The composition of the present invention may contain other ingredients.

The cosmetic composition in accordance with the invention may contain a variety of other ingredients including film forming polymers, pigments, waxes, oils, vitamins, and so on. Examples of such other ingredients include those described below.

A. Pigments

The composition of the invention may comprise about 0.05-30%, preferably about 0.1-25%, more preferably about 0.5-20% by weight of the total composition of one or more pigments which may be organic or inorganic. Examples of organic pigment families that may be used herein include azo, (including monoazo and diazo), fluoran, xanthene, indigoid, triphenylmethane, anthroquinone, pyrene, pyrazole, quinoline, quinoline, or metallic salts thereof. Preferred are D&C colors, FD&C colors, or Lakes of D&C or FD&C colors. The term "D&C" means drug and cosmetic colors that are approved for use in drugs and cosmetics by the FDA. The term "FD&C" means food, drug, and cosmetic colors which are approved for use in foods, drugs, and cosmetics by the FDA. Certified D&C and FD&C colors are listed in 21 CFR 74.101 et seq. and include the FD&C colors Blue 1, Blue 2, Green 3, Orange B, Citrus Red 2, Red 3, Red 4, Red 40, Yellow 5, Yellow 6, Blue 1, Blue 2; Orange B, Citrus Red 2; and the D&C colors Blue 4, Blue 9, Green 5, Green 6, Green 8, Orange 4, Orange 5, Orange 10, Orange 11, Red 6, Red 7, Red 17, Red 21, Red 22, Red 27, Red 28, Red 30, Red 31, Red 33, Red 34, Red 36, Red 39, Violet 2, Yellow 7, Yellow 8, Yellow 10, Yellow 11, Blue 4, Blue 6, Green 5, Green 6, Green 8, Orange 4, Orange 5, Orange 10, Orange 11, and so on. Suitable Lakes of D&C and FD&C colors are defined in 21 CFR 82.51. Particularly preferred are Lakes formed by the reaction of the organic pigment with a metallic salt such as aluminum, calcium, zirconium, barium, and the like. Suitable reds include pigments from the monoazo, disazo, fluoran, xanthene, or indigoid families or Lakes thereof, such as Red 4, 6, 7, 17, 21, 22, 27, 28, 30, 31, 33, 34, 36, and Red 40. Also suitable are Lakes of such red pigments. Typically the metal salts are aluminum, barium, and the like.

Suitable yellows include those where the yellow pigment is a pyrazole, monoazo, fluoran, xanthene, quinoline, or salt thereof, such as Yellow 5, 6, 7, 8, 10, and 11, as well as Lakes of such yellow pigments.

Suitable violets include those from the anthroquinone family, such as Violet 2 and Lakes thereof. Examples of orange pigments are Orange 4, 5, 10, 11, or Lakes thereof.

Suitable inorganic pigments include iron oxides such as red, blue, black, green, and yellow; titanium dioxide, bismuth oxychloride, and the like. Preferred are iron oxides. The iron oxides may be treated with hydrophobic agents such as silicone, lecithin, mineral oil, or similar materials, will cause the pigment to be hydrophobic or lipophilic in nature, exhibiting an affinity for oily phase ingredients.

B. Particulate Fillers

The composition may contain one or more particulate fillers, which are generally non-pigmentitious powdery materials. If so, suggested ranges are about 0.001-40%, preferably about 0.05-35%, more preferably about 0.1-30% by weight of the total composition. Preferably, the particulate fillers have particle sizes ranging from about 0.02 to 100, preferably 0.5 to 100, microns. Suitable particle fillers include titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silk powder, silica, talc, mica, zinc laurate, zinc myristate, zinc rosinate, alumina, attapulgite, calcium carbonate, calcium silicate, dextran, kaolin, nylon, silica silylate, sericite, soy flour, tin oxide, titanium hydroxide, trimagnesium phosphate, walnut shell powder, or mixtures thereof. The above mentioned powders may be surface treated with lecithin, amino acids, mineral oil, silicone oil or various other agents either alone or in combination, which coat the powder surface and render the particles more lipophilic in nature.

C. Oils

The composition may contain one or more oils, and if so in ranges from about 0.1-95%, preferably about 5-80%, more preferably about 10-75% by weight of the total composition. The term "oil" means a material that is a pourable liquid at room temperature. A variety of such oils are suitable including volatile oils, nonvolatile oils, and mixtures thereof.

1. Volatile Oils

The term "volatile" means that the oil has a measurable vapor pressure, or a vapor pressure of at least about 2 mm. of mercury at 20° C. The term "nonvolatile" means that the oil has a vapor pressure of less than about 2 mm. of mercury at 20° C. Suitable volatile oils generally have a viscosity of about 0.5 to 10 centipoise at 25° C. and include linear silicones, cyclic silicones, paraffinic hydrocarbons, or mixtures thereof.

(a). Volatile Silicones

Cyclic silicones (or cyclomethicones) are compounds of commerce.

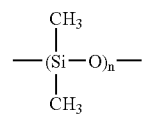

where n=3-6.

Linear volatile silicones in accordance with the invention have the general formula:

where n=0-7, preferably 0-5.

Linear and cyclic volatile silicones are available from various commercial sources including Siltech LLC, Dow Coming Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

(b). Paraffinic Hydrocarbons

Also suitable as the volatile oil are various straight or branched chain paraffinic hydrocarbons having 5 to 40 carbon atoms, more preferably 8-20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70-225, preferably 160 to 190 and a boiling point range of 30 to 320, preferably 60-260° C., and a viscosity of less than 10 cs. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable.

2. Nonvolatile Oils

The composition may also comprise one or more nonvolatile liquid oils such as silicones, esters, and the like. In the case where it is desired to make long wearing cosmetic products, if the nonvolatile oils are too heavy or greasy it may hamper the long wearing characteristics of the invention. In such a case, the viscosity of the nonvolatile oils, if present, should range from about 11-1000, preferably less than 100 centipoise, most preferably less than about 50 centipoise at 25° C. Examples of such oils include polyalkylsiloxanes, polyarylsiloxanes, and polyethersiloxanes. Examples of such nonvolatile silicones are disclosed in Cosmetics, Science and Technology 27-104 (Balsam and Sagarin ed. 1972); and U.S. Pat. Nos. 4,202,879 and 5,069,897, both of which are hereby incorporated by references. Further nonlimiting examples of such silicones include dimethicone, phenyl trimethicone, dimethicone copolyol, and so on.

Also suitable are lower viscosity organic liquids including saturated or unsaturated, substituted or unsubstituted branched or linear or cyclic organic compounds that are liquid under ambient conditions. Preferred organic liquids include those described in U.S. Pat. Nos. 5,505,937; 5,725,845; 5,019,375; and 6,214,329, all of which are incorporated by reference herein in their entirety.

If desired, the claimed composition may contain one or more nonvolatile oils. Such oils generally have a viscosity of greater than 10 centipoise at 25° C., and may range in viscosity up to 1,000,000 centipoise at 25° C. Such nonvolatile oils are preferably liquid at room temperature (e.g. 25° C.), and include those set forth below. In the event long-wearing or transfer resistant compositions are desired, if non-volatile oils are present, they are preferably of lower viscosity, e.g. ranging from about 10 to 100,000, preferably 10-50,000, more preferably 10-1000 centipoise at room temperature. Further examples of non volatile oils include those set forth below.

(a). Esters

Suitable esters are mono-, di-, and triesters. The composition may comprise one or more esters selected from the group, or mixtures thereof.

(i). Monoesters

Monoesters are defined as esters formed by the reaction of a monocarboxylic acid having the formula R—COOH, wherein R is a straight or branched chain saturated or unsaturated alkyl having 2 to 30 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups, and in one preferred embodiment of the invention the acid is an alpha hydroxy acid. Either one or both of the acid or alcohol may be a "fatty" acid or alcohol, ie. may have from about 6 to 22 carbon atoms. Examples of monoester oils that may be used in the compositions of the invention include hexyldecyl benzoate, hexyl laurate, hexadecyl isostearate, hexydecyl laurate, hexyldecyl octanoate, hexyldecyl oleate, hexyldecyl palmitate, hexyldecyl stearate, hexyldodecyl salicylate, hexyl isostearate, butyl acetate, butyl isostearate, butyl oleate, butyl octyl oleate, cetyl palmitate, ceyl octanoate, cetyl laurate, cetyl lactate, isostearyl isononanoate, cetyl isononanoate, cetyl stearate, stearyl lactate, stearyl octanoate, stearyl heptanoate, stearyl stearate, and so on. It is understood that in the above nomenclature, the first term indicates the alcohol and the second term indicates the acid in the reaction, i.e. stearyl octanoate is the reaction product of stearyl alcohol and octanoic acid.

(ii). Diesters

Suitable diesters that may be used in the compositions of the invention are the reaction product of a dicarboxylic acid and an aliphatic or aromatic alcohol. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. The aliphatic or aromatic alcohol may be substituted with one or more substitutents such as hydroxyl. Preferably, one or more of the acid or alcohol is a fatty acid or alcohol, i.e. contains 14-22 carbon atoms. The dicarboxylic acid may also be an alpha hydroxy acid. Examples of diester oils that may be used in the compositions of the invention include diisostearyl malate, neopentyl glycol dioctanoate, dibutyl sebacate, di-$C_{12-13}$ alkyl malate, dicetearyl dimer dilinoleate, dicetyl adipate, diusocetyl adipate, diisononyl adipate, diisostearyl dimer dilinoleate, disostearyl fumarate, diisostearyl malate, and so on.

(iii). Triesters

Suitable triesters comprise the reaction product of a tricarboxylic acid and an aliphatic or aromatic alcohol. As with the mono- and diesters mentioned above, the acid and alcohol contain 2 to 30 carbon atoms, and may be saturated or unsaturated, straight or branched chain, and, may be substituted with one or more hydroxyl groups. Preferably, one or more of the acid or alcohol is a fatty acid or alcohol containing 14 to 22 carbon atoms. Examples of triesters include triarachidin, tributyl citrate, triisostearyl citrate, tri C12-13 alkyl citrate, tricaprylin, tricaprylyl citrate, tridecyl behenate, trioctyldodecyl citrate, tridecyl behenate, tridecyl cocoate, tridecyl isononanoate, and so on.

(b). Hydrocarbon Oils.

It may be desirable to incorporate one or more non-volatile hydrocarbon oils into the claimed composition. The term "nonvolatile" means that the oil has a vapor pressure of less than about 2 mm. of mercury at 20° C.

Suitable nonvolatile hydrocarbon oils include isoparaffins and olefins having greater than 20 carbon atoms. Examples of such hydrocarbon oils include $C_{24-28}$ olefins, $C_{30-45}$ olefins, $C_{20-40}$ isoparaffins, hydrogenated polyisobutene, mineral oil, pentahydrosqualene, squalene, squalane, and mixtures thereof.

(c). Lanolin Oil

Also suitable for use in the composition is lanolin oil or derivatives thereof containing hydroxyl, alkyl, or acetyl groups, such as hydroxylated lanolin, isobutylated lanolin oil, acetylated lanolin, acetylated lanolin alcohol, and so on.

(d). Glyceryl Esters of Fatty Acids

The nonvolatile oil may also comprise naturally occurring glyceryl esters of fatty acids, or triglycerides. Both vegetable and animal sources may be used. Examples of such oils include castor oil, lanolin oil, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the oil are synthetic or semi-synthetic glyceryl esters, e.g. fatty acid mono-, di-, and triglycerides which are natural fats or oils that have been modified, for example, acetylated castor oil, or mono-, di- or triesters of polyols such as glyceryl stearate, diglyceryl diiosostearate, polyglyceryl-4 isostearate, polyglyceryl-6 ricinoleate, glyceryl dioleate, glyceryl diisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

(e). Nonvolatile Silicones

Nonvolatile silicone oils, both water soluble and water insoluble, are also suitable for use as the non-volatile oil. Such silicones preferably have a viscosity ranging from about 10 to 600,000 centistokes, preferably 20 to 100,000 centistokes at 25° C. Suitable water insoluble silicones include amine functional silicones such as amodimethicone; phenyl substituted silicones such as bisphenylhexamethicone, phenyl trimethicone, or polyphenylmethylsiloxane; dimethicone, alkyl substituted dimethicones, and mixtures thereof.

Water soluble, non-film forming silicones such as dimethicone copolyol, dimethiconol, and the like may be used. Such silicones are available from Dow Corning as the 3225C formulation aid, Dow 190 and 193 fluids, or similar products marketed by Goldschmidt under the ABIL tradename and Siltech LLC under the Silube tradename.

Also suitable as the oil are various fluorinated oils such as fluorinated silicones, fluorinated esters, or perfluoropolyethers. Particularly suitable are fluorosilicones such as trimethylsilyl endcapped fluorosilicone oil, polytrifluoropropyl-methylsiloxanes, and similar silicones such as those disclosed in U.S. Pat. No. 5,118,496 which is hereby incorporated by reference. Perfluoropolyethers like those disclosed in U.S. Pat. Nos. 5,183,589, 4,803,067, 5,183,588 all of which are hereby incorporated by reference, which are commercially available from Montefluos under the trademark Fomblin, are also suitable shine enhancers.

(f). Fluoroguerbet Esters

Fluoroguerbet esters are also suitable oils. The term "guerbet ester" means an ester which is formed by the reaction of a guerbet alcohol. Guerbet alcohols are well known in the art. One specific type is as follows:

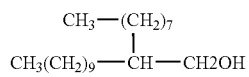

and a fluoroalcohol having the following general formula:

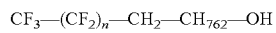

wherein n is from 3 to 40.
with a carboxylic acid having the general formula:

or

HOOC—R'—COOH wherein R' is a straight or branched chain alkyl.

Preferably, the guerbet ester is a fluoro-guerbet ester which is formed by the reaction of a guerbet alcohol and carboxylic acid (as defined above), and a fluoroalcohol having the following general formula:

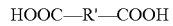

wherein n is from 3 to 40.

Examples of suitable fluoro guerbet esters are set forth in U.S. Pat. No. 5,488,121 to O'Lenick, which is hereby incorporated by reference. Suitable fluoro-guerbet esters are also set forth in U.S. Pat. No. 5,312,968 which is hereby incorporated by reference. One type of such an ester is fluorooctyldodecyl meadowfoamate, sold under the tradename Silube GME-F by Siltech LLC, Dacula Ga.

D. Additional Film Forming Polymers

The composition may contain one or more film forming polymers in addition to the linear silicone resin, and if so, ranges of about 0.1-35%, preferably 0.5-30%, more preferably 1-25% by weight of the total composition of one or more film forming polymers. The film forming polymer (or film former) may be water soluble or water insoluble. Suitable film forming polymers are those that, when the composition is applied to the desired surface, form a film on the surface to which the composition is applied when the liquid in the composition evaporates. This causes the film forming polymer to form a film which holds the other active ingredients in place with the network created by the hardened polymer. The term "soluble" means that the film forming polymer is soluble in the phase in question, and will form a single homogeneous phase when incorporated therein. For example, if the film forming polymer is oil soluble it will generally be soluble in the oil phase of the composition and when incorporated therein the oil and the polymer will form a single homogeneous phase with the oily phase ingredients. Similarly, if the film forming polymer is water soluble, if incorporated in the water phase the polymer and the water will form a single homogeneous phase. In the case where the compositions of the invention are in the emulsion form, it may also be possible for the emulsion to contain a film forming polymer that is soluble in one phase but is found dispersed in the other phase. For example, water soluble film forming polymer may be dispersed in the oil phase of the emulsion or an oil soluble polymer may be dispersed in the water phase of the emulsion. In short, any combination of film forming polymer and phase is suitable so long as the compositions are stable. The term "dispersible" means that the film forming polymer is readily dispersed in the liquid vehicle and forms a stable, heterogeneous composition where the dispersed polymer remains stable and suspended in the liquid vehicle and is compatible therewith (without settling out, for example).

A variety of film forming polymers may be suitable. Such polymers may be natural or synthetic and are further described below.

1. Synthetic Polymers (a). Copolymers of Silicone and Organic Moieties

One type of film forming polymer that may be used in the compositions of the invention is obtained by reacting silicone moieties with ethylenically unsaturated monomers. These copolymers may be water soluble or oil soluble depending on the substituents that are found on the polymer. The resulting copolymers may be graft or block copolymers. The term "graft copolymer" is familiar to one of ordinary skill in polymer science and is used herein to describe the copolymers which result by adding or "grafting" polymeric side chain moieties (i.e. "grafts") onto another polymeric moiety referred to as the "backbone". The backbone may have a higher molecular weight than the grafts. Thus, graft copolymers can be described as polymers having pendant polymeric side chains, and which are formed from the "grafting" or incorporation of polymeric side chains onto or into a polymer backbone. The polymer backbone can be a homopolymer or a copolymer. The graft copolymers are derived from a variety of monomer units.

One type of polymer that may be used as the film forming polymer is a vinyl-silicone graft or block copolymer. Such material is outlines in U.S. Patent Publication 2004/0180020A1 published Sep. 16, 2004 paragraph [0082] to [0094] incorporated herein by reference.

Another type of such a polymer comprises a vinyl, methacrylic, or acrylic backbone with pendant siloxane groups and pendant fluorochemical groups. Such polymers preferably comprise repeating A, C, D and optionally B monomers. Such material is outlines in U.S. Patent Publication 2004/0180020A1 published Sep. 16, 2004 paragraph [0095] to [0107] incorporated herein by reference.

Such polymers and their manufacture are disclosed in U.S. Pat. Nos. 5,209,924 and 4,972,037, which are hereby incorporated by reference. These polymers may be water soluble or oil soluble depending on the polymeric substituents.

Another suitable silicone acrylate copolymer is a polymer having a vinyl, methacrylic, or acrylic polymeric backbone with pendant siloxane groups. Such polymers as disclosed in U.S. Pat. Nos. 4,693,935, 4,981,903, 4,981,902, and which are hereby incorporated by reference. Preferably, these polymers are comprised of A, C, and optionally B monomers are outlined in U.S. Patent Publication 2004/0180020A1 published Sep. 16, 2004 paragraph [0109] to [0122] incorporated herein by reference.

Examples of other suitable copolymers that may be used herein, and their method of manufacture, are described in detail in U.S. Pat. No. 4,693,935, Mazurek, U.S. Pat. No. 4,728,571, and Clemens et al., both of which are incorporated herein by reference. Additional grafted polymers are also disclosed in EPO Application 90307528.1, published as EPO Application 0 408 311, U.S. Pat. No. 5,061,481, Suzuki et al., U.S. Pat. No. 5,106,609, Bolich et al., U.S. Pat. No. 5,100,658, Bolich et al., U.S. Pat. No. 5,100,657, Ansher-Jackson, et al., U.S. Pat. No. 5,104,646, Bolich et al., U.S. Pat. No. 5,618,524, issued Apr. 8, 1997, all of which are incorporated by reference herein in their entirety.

(b). Polymers from Ethylenically Unsaturated Monomers

Also suitable for use as film forming polymers are polymers made by polymerizing one or more ethylenically unsaturated monomers either alone or in combination with various types of organic groups, including but not limited to urethane, amides, polypropylene glycols, etc. The final polymer may be a homopolymer, copolymer, terpolymer, or graft or block copolymer, and may contain monomeric units such as acrylic acid, methacrylic acid or their simple esters, styrene, ethylenically unsaturated monomer units such as ethylene, propylene, butylene, etc., vinyl monomers such as vinyl chloride, styrene, and so on. Such polymers may be water soluble or dispersible, or oil soluble or dispersible in oil.

One type of suitable polymer includes those which contain monomers which are esters of acrylic acid or methacrylic acid, including aliphatic esters of methacrylic acid like those obtained with the esterification of methacrylic acid or acrylic acid with an aliphatic alcohol of 1 to 30, preferably 2 to 20, more preferably 2 to 8 carbon atoms. If desired, the aliphatic alcohol may have one or more hydroxy groups. Also suitable are methacrylic acid or acrylic acid esters esterified with moieties containing alicyclic or bicyclic rings such as cyclohexyl or isobornyl, for example.

The ethylenically unsaturated monomer may be mono-, di-, tri-, or polyfunctional as regards the addition-polymerizable ethylenic bonds. A variety of ethylenically unsaturated monomers are suitable.

Examples of suitable monofunctional ethylenically unsaturated monomers are material outlined in U.S. Patent Publication 2004/0180020A1 published Sep. 16, 2004 paragraph [0129] to [0144] incorporated herein by reference.

The polymers used in the compositions of the invention can be prepared by conventional free radical polymerization techniques in which the monomer, solvent, and polymerization initiator are charged over a 1-24 hour period of time, preferably 2-8 hours, into a conventional polymerization reactor in which the constituents are heated to about 60-175° C., preferably 80-100° C. The polymers may also be made by emulsion polymerization or suspension polymerization using conventional techniques. Also anionic polymerization or Group Transfer Polymerization (GTP) is another method by which the copolymers used in the invention may be made. GTP is well known in the art and disclosed in U.S. Pat. Nos. 4,414,372; 4,417,034; 4,508,880; 4,524,196; 4,581,428; 4,588,795; 4,598,161; 4,605,716; 4,605,716; 4,622,372; 4,656,233; 4,711,942; 4,681,918; and 4,822,859; all of which are hereby incorporated by reference.

(c). Silicone Polymers

Also suitable are various types of water soluble or water insoluble (oil soluble) high molecular weight silicone polymers such as silicone gums, resins, and the like.

Suitable silicone resins include siloxy silicate polymers having the following general formula:

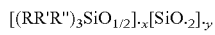

[(RR'R")$_3$SiO$_{1/2}$]$_{-x}$[SiO$_{-2}$]$_{-y}$ wherein R, R' and R" are each independently a C$_{1-10}$ straight or branched chain alkyl or phenyl, and x and y are such that the ratio of (RR'R")$_3$SiO$_{1/2}$ units to SiO$_{-2}$ units is 0.5 to 1 to 1.5 to 1.

Preferably R, R' and R" are a C$_{1-6}$ alkyl, and more preferably are methyl and x and y are such that the ratio of (CH$_3$)$_{-3}$SiO$_{-1/2}$ units to SiO$_2$ units is 0.75 to 1. Most preferred is this trimethylsiloxy silicate containing 2.4 to 2.9 weight percent hydroxyl groups which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename 749 Fluid, which is a blend of about 40-60% volatile silicone and 40-60% trimethylsiloxy silicate. Dow Corning 749 fluid in particular, is a fluid containing about 50% trimethylsiloxy silicate and about 50% cyclomethicone. The fluid has a viscosity of 200-700 centipoise at 25° C., a specific gravity of 1.00 to 1.10 at 25° C., and a refractive index of 1.40-1.41. A similar siloxysilicate resin is available from GE Silicones under the tradename SR1000 and is a fine particulate solid material.

Another type of silicone resin is referred to as a T or MT resin, and has the general formula:

(R$_1$SiO$_{3/2}$)$_{-x}$ where x ranges from about 1 to 100,000, preferably about 1-50,000, more preferably about 1-10,000, and wherein R$_1$ is independently C$_{1-30}$, preferably C$_{-1-10}$, more preferably C$_{1-4}$ straight or branched chain alkyl, which may be substituted with phenyl or one or more hydroxyl groups; phenyl; alkoxy (preferably C$_{1-22}$, more preferably C$_{-1-6}$); or hydrogen. Typically T or MT silicones are referred to as silsesquioxanes, and in the case where M units are present methylsilsesquioxanes. One type of such resin is manufactured by Wacker Chemie under the Resin MK designation. This polysilsesquioxane is a polymer comprise of T units and, optionally one or more D (preferably dimethylsiloxy) units. This particularly polymer may have ends capped with ethoxy groups, and/or hydroxyl groups, which may be due to how the polymers are made, e.g. condensation in aqueous or alcoholic media. Other suitable polysilsesquioxanes that may be used as the film forming polymer include those manufactured by Shin-Etsu Silicones and include the "KR" series, e.g. KR-220L, 242A, and so on. These particular silicone resins may contain endcap units that are hydroxyl or alkoxy groups which may be present due to the manner in which such resins are manufactured.

Another type of silicone resin suitable for use in the invention comprises the silicone esters set forth in U.S. Pat. No. 5,725,845 which is hereby incorporated by reference in its entirety. Other polymers that can enhance adhesion to skin include silicone esters comprising units of the general formula disclosed in U.S. Patent Publication 2004/0180020A1 published Sep. 16, 2004 paragraph [0152] to [0153] incorporated herein by reference.

Preferably the silicone ester will have a melting point of no higher than about 90° C. It can be a liquid or solid at room temperature. Preferably it will have a waxy feel and a molecular weight of no more than about 100,000 Daltons.

Silicone esters having the above formula are disclosed in U.S. Pat. No. 4,725,658 and U.S. Pat. No. 5,334,737, which are hereby incorporated by reference. Preferred silicone esters are the liquid siloxy silicates disclosed in U.S. Pat. No. 5,334,737, e.g. diisostearoyl trimethylolpropane siloxysilicate (prepared in Examples 9 and 14 of this patent), and dilauroyl trimethylolpropane siloxy silicate (prepared in Example 5 of the patent), which are commercially available from General Electric under the tradenames SF 1318 and SF 1312, respectively.

Silicone gums or other types of silicone solids may be used provided they are soluble in the liquid vehicle. Examples of silicone gums include those set forth in U.S. Pat. No. 6,139,823, which is hereby incorporated by reference. Preferred gums have a 600,000 to 1,000,000 centipoise at 25° C.

2. Natural Polymers

Also suitable for use are one or more naturally occurring water soluble or oil soluble polymeric materials such as resinous plant extracts including such as rosin, shellac, and the like.

E. Plasticizers

It may be desirable to incorporate one more plasticizers into the composition. Plasticizers may improve the spreadability and application of the composition to the surface to which it is applied and in some cases will interact with the film forming polymer to make it more flexible. If present, the plasticizer may be found in the oil or water phase if the composition of the invention is in the form of an emulsion, and in the oil or lipophilic phase if the composition is in the anhydrous ° form. Suggested ranges of plasticizers range from about 0.01-20%, preferably about 0.05-15%, more preferably about 0.1-10% by weight of the total composition. A variety of plasticizers are suitable including Suitable plasticizers include glyceryl, glycol, and citrate esters as disclosed in U.S. Pat. No. 5,066,484, which is hereby incorporated by reference. Examples of such esters include glyceryl tribenzoate, glyceryl triacetate, acetyl tributyl citrate, dipropylene glycol dibenzoate, and the like.

F. Viscosity Modifiers

It may also be desirable to include one or more viscosity modifiers or thickeners in the composition. Suggested ranges of such viscosity modifiers are about 0.01-60%, preferably about 0.05-50%, more preferably about 0.1-45% by weight of the total composition.

One type of viscosity modifier includes natural or synthetic montmorillonite minerals such as hectorite, bentonite, and quaternized derivatives thereof which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like. Particularly preferred is Quaternium-18 hectorite.

Also suitable as the viscosity modifier are various polymeric compounds known in the art as associative thickeners. Suitable associative thickeners generally contain a hydrophilic backbone and hydrophobic side groups. Examples of such thickeners include polyacrylates with hydrophobic side groups, cellulose ethers with hydrophobic side groups, polyurethane thickeners. Examples of hydrophobic side groups are long chain alkyl groups such as dodecyl, hexadecyl, or octadecyl; alkylaryl groups such as octylphenyl or nonyphenyl Another type of viscosity modifier that may be used in the compositions are silicas, silicates, silica silylate, and derivatives thereof. These silicas and silicates are generally found in the particulate form. Particularly preferred is silica.

The viscosity modifers may also be water soluble or water insoluble (e.g. oil soluble) and form part of the oil phase or the water phase.

Also suitable as viscosity modifiers are one or more waxes. A variety of waxes are suitable including animal, vegetable, mineral, or silicone waxes. Generally such waxes have a melting point ranging from about 28 to 125° C., preferably about 30 to 100° C. Examples of waxes include acacia, beeswax, ceresin, cetyl esters, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, candelilla, grape wax, and polyalkylene glycol derivatives thereof such as PEG6-20 beeswax, or PEG-12 carnauba wax.

Also suitable are various types of silicone waxes, referred to as alkyl silicones, which are polymers that comprise repeating dimethylsiloxy units in combination with one or more methyl-long chain alkyl siloxy units wherein the long chain alkyl is generally a fatty chain that provides a wax-like characteristic to the silicone. Such silicones include, but are not limited to stearoxydimethicone, behenoxy dimethicone, stearyl dimethicone, cetearyl dimethicone, and so on. Suitable waxes are set forth in U.S. Pat. No. 5,725,845, which is hereby incorporated by reference in its entirety. Preferred ranges of wax are from about 0.01-75%, preferably about 1-65% by weight of the total composition.

G. Surfactants

The compositions of the invention may comprise about 0.01-20%, preferably about 0.1-15%, more preferably about 0.5-10% by weight of the total composition of a surfactant. Surfactants may be used in both anhydrous and emulsion based compositions. The surfactant may be nonionic, although if the composition is in the form of a shampoo or conditioner it will preferably contain anionic or cationic surfactants, respectively.

Suitable nonionic surfactants or emulsifiers include alkoxylated alcohols, or ethers, formed by the reaction of an alcohol with an alkylene oxide, usually ethylene or propylene oxide. Preferably the alcohol is a fatty alcohol having 6 to 30 carbon atoms. Examples of such ingredients include Beheneth 5-30, which is formed by the reaction of behenyl alcohol and ethylene oxide where the number of repeated ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on. Other alkoxylated alcohols are formed by the reaction of fatty acids and mono-, di- or polyhydric alcohols with an alkylene oxide. For example, the reaction products of $C_{-6-30}$ fatty carboxylic acids and polyhydric alcohols which are monosaccharides such as glucose, galactose, methyl glucose, and the like, with an alkoxylated alcohol. Preferred are alkoxylated alcohols which are formed by the reaction of stearic acid, methyl glucose, and ethoxylated alcohol, otherwise known as PEG-20 methyl glucose sesquiisostearate.

Also suitable as the nonionic surfactant are alkyoxylated carboxylic acids, which are formed by the reaction of a carboxylic acid with an alkylene oxide or with a polymeric ether. The resulting products have the general formula disclosed in U.S. Patent Publication 2004/0180020A1 published Sep. 16, 2004 paragraph [0172] incorporated herein by reference.

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20-85, sorbitan oleate, sorbitan palmitate, sorbitan sesquiisostearate, sorbitan stearate, and so on.

Also suitable as nonionic surfactants are silicone surfactants, which are defined as silicone polymers, which have at least one hydrophilic radical and at least one lipophilic radical. The silicone surfactant used in the compositions of the invention are organosiloxane polymers that may be a liquid or solid at room temperature. The organosiloxane surfactant is generally a water-in-oil or oil-in-water type surfactant which is, and has an Hydrophile/Lipophile Balance (HLB) of 2 to 18. Preferably the organosiloxane is a nonionic surfactant having an HLB of 2 to 12, preferably 2 to 10, most preferably 4 to 6. The HLB of a nonionic surfactant is the balance between the hydrophilic and lipophilic portions of the surfactant.

Examples of silicone surfactants are those sold by Siltech LLC under the Silsurf tradename, Dow Coming under the tradename Dow Coming 3225C Formulation Aid, Dow Coming 190 Surfactant, Dow Coming 193 Surfactant, Dow Coming Q2-5200, and the like are also suitable. In addition, surfactants sold under the tradename Silwet by Union Carbide, and surfactants sold by Troy Corporation under the Troysol tradename, those sold by Taiwan Surfactant Co. under the tradename Ablusoft, those sold by Hoechst under the tradename Arkophob, are also suitable for use in the invention. Such types of silicone surfactants are generally referred to as dimethicone copolyols or alkyl dimethicone copolyols.

Suitable cationic, anionic, zwitterionic, and amphoteric surfactants are disclosed in U.S. Pat. No. 5,534,265, which is hereby incorporated by reference in its entirety.

H. Sunscreens

If desired, the compositions of the invention may contain 0.001-20%, preferably 0.01-10%, more preferably 0.05-8% of one or more sunscreens. A sunscreen is defined as an ingredient that absorbs at least 85 percent of the light in the UV range at wavelengths from 290 to 320 nanometers, but transmits UV light at wavelengths longer than 320 nanometers. Sunscreens generally work in one of two ways. Particulate materials, such as zinc oxide or titanium dioxide, as mentioned above, physically block ultraviolet radiation. Chemical sunscreens, on the other hand, operate by chemically reacting upon exposure to UV radiation. Suitable sunscreens that may be included in the compositions of the invention are set forth on page 582 of the CTFA Cosmetic Ingredient Handbook, Second Edition, 1992, as well as U.S. Pat. No. 5,620,965, both of which are hereby incorporated by reference. Further examples of chemical and physical sunscreens include those set forth below.

1. UVA Chemical Sunscreens

The term "UVA sunscreen" means a chemical compound that blocks UV radiation in the wavelength range of about 320 to 400 nm.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isorpoyl-4'-methoxydibenzoymet-hane, 2-metyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

The claimed compositions may contain from about 0.001-20%, preferably 0.005-5%, more preferably about 0.005-3% by weight of the composition of UVA sunscreen. In one preferred embodiment of the invention the UVA sunscreen is Avobenzone, and it is present at not greater than about 3% by weight of the total composition.

2. UVB Chemical Sunscreens

The term "UVB sunscreen" means a compound that blocks UV radiation in the wavelength range of from about 290 to 320 nm. A variety of UVB chemical sunscreens exist including .alpha.-cyano-.beta.,,beta.-diphenyl acrylic acid esters as set forth in U.S. Pat. No. 3,215,724, which is hereby incorporated by reference in its entirety. Particularly preferred is Octocrylene, which is 2-ethylhexyl 2-cyano-3,3-diphenylacrylate. Preferred is where the composition contains no more than about 10% by weight of the total composition of octocrylene. Suitable amounts range from about 0.001-10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety.

Also suitable are cinnamate derivatives.

3. Physical Sunscreens

The composition may also contain one or more physical sunscreens. The term "physical sunscreen" means a material that is generally particulate in form that is able to block UV rays by forming an actual physical block on the skin. Examples of particulates that serve as solid physical sunblocks include titanium dioxide, zinc oxide and the like in particle sizes ranging from about 0.001-50 microns, preferably less than 1 micron.

J. Vitamins and Antioxidants

The compositions of the invention may contain vitamins and/or coenzymes, as well as antioxidants. If so, 0.001-10%, preferably 0.01-8%, more preferably 0.05-5% by weight of the total composition are suggested. Suitable vitamins include ascorbic acid and derivatives thereof, the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

K. Humectants

If desired, the compositions of the invention comprise about 0.01-30%, preferably about 0.5-25%, more preferably about 1-20% by weight of the total composition of one or more humectants. Suitable humectants include di- or polyhydric alcohols such as glycols, sugars, and similar materials. Suitable glycols include alkylene glycols such as propylene, ethylene, or butylene glycol; or polymeric alkylene glycols such as polyethylene and polypropylene glycols, including PEG 4-240, which are polyethylene glycols having from 4 to 240 repeating ethylene oxide units. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on.

L. Other Botanical Extracts

It may be desirable to include one or more additional botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including acacia (dealbata, famesiana, senegal), acer saccharinum (sugar maple), acidopholus, acorus, aesculus, agaricus, agave, agrimonia, algae, aloe, citrus, brassica, cinnamon, orange, apple, blueberry, cranberry, peach, pear, lemon, lime, pea, seaweed, green tea, chamomile, willowbark, mulberry, poppy, and those set forth on pages 1646 through 1660 of the CTFA Cosmetic Ingredient Handbook, Eighth Edition, Volume 2.

M. Water Soluble Gellants

If the composition is in the emulsion form, it may be desirable to include other water soluble gellants in the water phase of the composition to provide thickening. Such gellants may be included a range of about 0.1-20%, preferably about 1-18%, more preferably about 2-10% by weight of the total composition is suggested, if present. Suitable gellants include soaps, i.e. salts of water insoluble fatty acids with various bases. Examples of soaps include the aluminum, calcium, magnesium, potassium, sodium, or zinc salts of $C_{6-30}$, preferably $C_{10-22}$ fatty acids.

Also suitable are hydrocolloids such as gellan gum, gum arabic, carrageenan, and those set forth in U.S. Pat. No. 6,197,319 which is hereby incorporated by reference in its entirety.

N. Preservatives

The composition may contain 0.001-8%, preferably 0.01-6%, more preferably 0.05-5% by weight of the total composition of preservatives. A variety of preservatives are suitable, including such as benzoic acid, benzyl alcohol, benzylhemiformal, benzylparaben, 5-bromo-5-nitro-1,3-diox-ane, 2-bromo-2-nitropropane-1,3-diol, butyl paraben, phenoxyethanol, methyl paraben, propyl paraben, diazolidinyl urea, calcium benzoate, calcium propionate, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and all of those disclosed on pages 570 to 571 of the CTFA Cosmetic Ingredient Handbook, Second Edition, 1992, which is hereby incorporated by reference.

O. Emulsion Stabilizers

If the composition of the invention is in the emulsion form, it may be desirable to incorporate one or more emulsion stabilizers in the composition. If so, suggested ranges are about 0.0001-5%, preferably about 0.0005-3%, more preferably about 0.001-2% by weight of the total composition. Suitable emulsion stabilizers include salts of alkali or alkaline earth metal chlorides or hydroxides, such as sodium chloride, potassium chloride, and the like.

III. Forms of the Cosmetic Compositions

The cosmetic compositions in accordance with the invention may be in a variety of forms include any type of cosmetic composition applied to keratinous surfaces for the purpose of coloring, conditioning, or otherwise beautifying the keratinous surface.

A. Foundation Makeup Color Cosmetics

Foundation makeup or color cosmetics such as eyeshadow, blush, concealer, or eyeliner compositions in the liquid, cream, solid, or stick form. Suitable foundation makeup compositions may be water-in-oil or oil-in-water emulsions. Such compositions generally comprise about:

0.001-90% linear silicone resin,
0.5-95% water,
0.5-25% particulate matter,
0.01-20% surfactant, and
0.1-95% nonvolatile or volatile oil.

In addition, these composition may further contain ingredients selected from the group of humectants, preservatives, gellants, and all of the ingredients as set forth above in the ranges set forth herein.

Various anhydrous color cosmetic products may also be suitable, such as blush, powder, lipsticks, eyeshadows, and the like. Such anhydrous color cosmetic compositions may generally comprise about:

0.001-80% linear silicone resin,
0.1-99% oil,
0.1-80% particulate matter; and optionally
0.001-50% thickening agent.

The compositions may additionally contain the various other ingredients set forth above and in the ranges taught.

Preferably, the compositions are in the form of a lipcolor or lipstick which may be a composition for coloring the lips that is in liquid, semi-solid, or solid form.

Alternatively, the composition may be in the form of a base lip color, which is a lip color applied to the lips as a basecoat to provide color, followed by application of a separate gloss coat which comprises one or more oils or waxes that provide shine, moisturization, or similar benefits to the layers applied to the lips. Examples of such lip compositions and topcoats are disclosed in U.S. patent application Ser. No. 2002/0159960, entitled "Method for Improving the Properties of Transfer Resistant Lip Compositions and Related Compositions and Articles", claiming priority from provisional application No. 60/271,849, filed Feb. 27, 2001; which is hereby incorporated by reference in its entirety.

B. Lotions, Creams, Gels, and Sunscreens

The cosmetic compositions of the invention may be in the form of lotions, gels or sunscreens. Suitable skin care lotions and creams are in the emulsion form, and may be water-in-oil or oil-in-water emulsions, preferably oil-in-water emulsions. Creams, lotions, and/or may contain the following ranges of ingredients:

about 0.001-80% of the linear silicone resin,
about 0.1-90% oil, and
about 0.01-20% surfactant.

C. Skin and Hair Cleansing and Conditioning Compositions

Skin and hair cleansing and conditioning compositions such as facial cleansers, shampoos, hair conditioners and the like are also suitable cosmetic compositions in accordance with the invention.

Generally skin and hair cleansing compositions comprise about:

0.001-90% of the linear silicone resin,
1-95% water, and
0.1-40% surfactant, preferably an anionic, amphoteric, or zwitterionic surfactant.
0.01-40% oil.

Suitable hair conditioner compositions comprise:
0.001-80% of the linear silicone resin,
0.1-20% cationic surfactant,
0.1-30% fatty alcohol,
0.001-10% nonionic surfactant, and
5-95% water.

Suitable cationic and nonionic surfactants are as mentioned herein. Examples of suitable fatty alcohols include those having the general formula R—OH, wherein R is a $C_{6-30}$ straight or branched chain, saturated or unsaturated alkyl.

D. Nail Enamel Compositions

The cosmetically acceptable carrier for use may also comprise nail enamel compositions. Such compositions generally comprise:

0.001-90% of the linear silicone resin,
0.01-80% solvent,
0.001-40% particulate matter, and optionally 0.01-40% of one or more polymers such as cellulosic polymers, acrylate polymers, and the like.

Suitable solvents include acetone, alkyl acetates such as ethyl acetate butyl acetate and the like, alkyl ethers such as propylene glycol monomethyl ether, and the like.

The invention will be further described in connection with the following examples which are set forth for the purposes of illustration only.

EXAMPLES

Raw Materials

Silanic Hydrogen Compounds (Examples 1-10)

Silanic hydrogen compounds are commercially available from Siltech Corporation Toronto Canada. They conform to the following structure

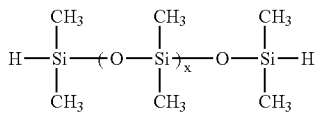

wherein;

x is an integer ranging from 0 to 5000.

| Example | x |
|---|---|
| 1 | 0 |
| 2 | 20 |
| 3 | 50 |
| 4 | 75 |
| 5 | 100 |
| 6 | 125 |
| 7 | 200 |
| 8 | 500 |
| 9 | 1000 |
| 10 | 2000 |

Vinyl Reactive Compounds (Examples 11-20)

Vinyl reactive compounds are commercially available from Siltech Corporation Toronto Canada. They conform to the following structure

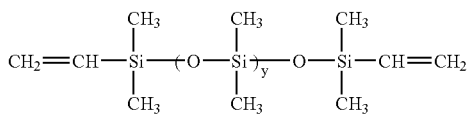

wherein;

y is an integer ranging from 0 to 2000.

| Example | y |
|---|---|
| 11 | 2000 |
| 12 | 1000 |
| 13 | 500 |
| 14 | 200 |
| 15 | 125 |

-continued

| Example | y |
|---|---|
| 16 | 100 |
| 17 | 75 |
| 18 | 50 |
| 19 | 20 |
| 20 | 0 |

Hydrosilylation Compounds of the Present Invention

Hydrosilylation Solvents (Examples 21-24)

The hydrosilylation reactions are advantageously run in a volatile solvent, which can later distilled off is desired. It is also a practice to sell the products in solvent.

| Example | Description |
|---|---|
| 21 | isododecane |
| 22 | cyclomethicone |
| 23 | polydimethyl siloxane 350 viscosity (Siltech F-350) |

Hydrosilylation

Hydrosilylation is a process that reacts terminal vinyl compounds with silanic hydrogen to obtain a Si—C bond. References to this reaction, incorporated herein by reference, include:

U.S. Pat. Nos. 3,715,334 and 3,775,452 to Karstedt, shows the use of Pt(O) complex with vinylsilicon siloxane ligands as an active hydrosilylation catalyst.

Additional platinum complexes, such as complexes with platinum halides are shown by, U.S. Pat. No. 3,159,601 Ashby and, U.S. Pat. No. 3,220,972, to Lamoreaux.

Another hydrosilylation catalyst is shown by Fish, U.S. Pat. No. 3,576,027. Fish prepares a platinum(IV) catalyst by reacting crystalline platinum(IV) chloroplatinic acid and organic silane or siloxane to form a stable reactive platinum hydrosilylation catalyst.

General Procedure

To the specified number of grams of the specified solvent is added the specified number of grams of the specified silanic hydrogen compound. The mass is mixed well. To that mixture is added the specified number of grams of the specified vinyl compound. The reaction mass is mixed well until homogeneous. To that mixture is added 0.1% Karstedt catalyst, which is commercially available from Geleste. The reaction mass will thicken over 4 hours. Once the maximum viscosity is reached the reaction is considered complete. The solvent may be distilled off or the product may be sold as prepared without additional purification.

EXAMPLES 25-34

| Example | Vinyl compound Example | Grams | Silanic Hydrogen Example | Grams | Solvent Example | Grams |
|---|---|---|---|---|---|---|
| 25 | 11 | 99.91 | 1 | 0.1 | 21 | 2000.0 |
| 26 | 12 | 97.87 | 2 | 2.34 | 22 | 2000.0 |
| 27 | 13 | 90.65 | 3 | 10.28 | 23 | 1441.8 |
| 28 | 14 | 72.5 | 4 | 30.25 | 21 | 1028.0 |
| 29 | 15 | 55.6 | 5 | 48.84 | 22 | 1305.5 |
| 30 | 16 | 44.7 | 6 | 60.83 | 23 | 1407.0 |
| 31 | 17 | 27.75 | 7 | 79.47 | 21 | 2145.0 |
| 32 | 18 | 9.47 | 8 | 99.58 | 21 | 1560.0 |
| 33 | 19 | 2.2 | 9 | 107.6 | 23 | 1100.0 |
| 34 | 20 | 0.13 | 10 | 109.9 | 22 | 1695.0 |

Applications Examples

Non-limiting examples of the use in the resins of the present invention in cosmetic lip care applications includes:

Cosmetic Applications-Lip

| Ingredient | % W/T | | | | | | | |
|---|---|---|---|---|---|---|---|---|
| Phase A | A | B | C | D | E | F | G | H |
| Example 28 | 99.30 | | | | | | | |
| Example 25 | | 99.30 | | | | | | |
| Example 30 | | | 99.30 | | | | | |
| Example 26 | | | | 99.30 | | | | |
| Example 27 | | | | | 99.30 | | | |
| Example 31 | | | | | | 99.30 | | |
| Example 26 | | | | | | | 99.30 | |
| Example 32 | | | | | | | | 99.30 |
| Mica, Titanium Dioxide | 0.30 | 0.30 | 0.30 | 0.30 | 0.30 | 0.30 | 0.30 | 0.30 |
| Mica, Titanium Dioxide and Iron Oxides | 0.15 | 0.15 | 0.15 | 0.15 | 0.15 | 0.15 | 0.15 | 0.15 |
| Calcium Aluminum Borosilicate Titanium Dioxide | 0.25 | 0.25 | 0.25 | 0.25 | 0.25 | 0.25 | 0.25 | 0.25 |
| Total | 100.00 | 100.00 | 100.00 | 100.00 | 100.00 | 100.00 | 100.00 | 100.00 |

PROCEDURE
Mix all ingredients at room temperature with proper blending

Additional non-limiting examples of the use in the resins of the present invention in cosmetic lip care applications includes:

Cosmetic Applications-Eyes

| Ingredient | % W/T | | | | | | | |
|---|---|---|---|---|---|---|---|---|
| Phase A | A | B | C | D | E | F | G | H |
| Calcium Aluminium Borosilicate | 25.00 | 25.00 | 25.00 | 25.00 | 23.00 | 23.00 | 23.00 | 23.00 |
| Iron Oxide | 1.00 | 1.00 | 1.00 | 1.00 | 1.00 | 1.00 | 1.00 | 1.00 |
| Manganese Violet | 0.35 | 0.35 | 0.35 | 0.35 | 0.35 | 0.35 | 0.35 | 0.35 |
| Phase B | | | | | | | | |
| Mica, Titanium Dioxide | 12.00 | 12.00 | 12.00 | 12.00 | 12.00 | 12.00 | 12.00 | 12.00 |
| Phase C | | | | | | | | |
| Carnauba wax, beeswax Dipentaerythrityl Hexacapryllate/Hexacaprate | 4.00 | 4.00 | 4.00 | 4.00 | 4.00 | 4.00 | 4.00 | 4.00 |
| Isododecane, Quaternium-18, Hectorite | 1.00 | 1.00 | 1.00 | 1.00 | 1.00 | 1.00 | 1.00 | 1.00 |
| Propylene Carbonate, | 4.00 | 4.00 | 4.00 | 4.00 | 4.00 | 4.00 | 4.00 | 4.00 |
| Example 28 | 52.65 | 37.65 | 42.65 | 37.65 | 44.65 | 39.65 | 44.65 | 39.65 |
| Example 25 | | 15.00 | | | | | | |
| Example 30 | | | 10.00 | | | | | |

-continued

| | Cosmetic Applications-Eyes | | | | | | | |
|---|---|---|---|---|---|---|---|---|
| | % W/T | | | | | | | |
| Ingredient | A | B | C | D | E | F | G | H |
| Example 26 | | | | 15.00 | | | | |
| Example 27 | | | | | 10.00 | | | |
| Example 31 | | | | | | 15.00 | | |
| Example 26 | | | | | | | 10.00 | |
| Example 32 | | | | | | | | 15.00 |
| Total | 100.00 | 100.00 | 100.00 | 100.00 | 100.00 | 100.00 | 100.00 | 100.00 |

1. Pre-mix Phase A in an osterizer.
2. Check the pigment dispersion
3. Repeat the process if needed.
4. Combine Phase C and heat to 80°-85° C.
5. Add Phase B to Phase C.
6. Add premixed Phase A to Phase B & C mixtures. Mix well.
7. Maintain the temperature while mixing.
8. Add Phase D to the batch and continue mixing.
9. Pour at 80°-75° C. in a mold.

In addition to their film forming properties, the resins of the present invention when applied to the skin have additional notable cosmetic properties and can endow the makeup or care product with at least one property chosen from properties of, for example, gloss, lubricity on application, comfort, color retention over time and after challenge, gloss retention over time, non-migration, outline definition and color intensity.

The composition disclosed herein may, for example, constitute a makeup product for the body, lips or epidermal derivatives of humans which can have properties of, for example, non-therapeutic treatment and/or care. In one embodiment, the composition disclosed herein constitutes a lipstick or lip-gloss, a blusher or eye shadow, a tattooing product, a mascara, an eyeliner, a nail varnish, an artificial tanning product for the skin or a hair care or hair coloring product.

The present inventors have obtained, surprisingly, a composition comprising at least one resin described resulting in a film which is glossy, comfortable and does not migrate. Moreover, the composition's color intensity can be much better than that of the prior art compositions.

The resins further exhibit effective dispersion of the pigments and/or fillers present in the composition; it does not exude when in stick form; it can have good properties of spreading and lubricity; and, moreover, it can endow the deposited film with sharply defined outlines and with properties of effective gloss retention and color retention over time (no color fading for at least three hours, uniform disappearance of the makeup). It can be, furthermore, stable, for example, for a number of months at ambient temperature (25° C. for more than a year) and can also be stable to heat (470 C. for 2 months) and to ultraviolet light without breakdown or odor over time.

Formulation Examples

Formulation Example 1

An emulsion mascara composition was prepared as follows:

| w/w % | Material |
|---|---|
| 1.75 | *Acacia Senegal* gum |
| 2.25 | Triethanolamine |
| 0.20 | Lecithin/polysorbate 20/sorbitan laurate/propylene |
| 0.20 | Glycol stearate/propylene glycol laurate Simethicone |
| 0.20 | Hydroxyethylcellulose |
| 0.50 | Panthenol |
| 1.50 | Nylon-12 |
| 0.30 | Methylparaben |
| 0.80 | Polyethylene |
| 9.00 | Iron oxides |
| 3.00 | Polysilicone 6 |
| 3.00 | Isododecane |
| 2.00 | Nylon 611/dimethicone copolymer/PPG-3 |
| 5.60 | myristyl ether Stearic acid |
| 10.80 | Paraffin |
| 2.80 | Beeswax |
| 2.30 | Glyceryl stearate |
| 1.00 | Phenoxyethanol |
| 0.10 | Propyl paraben |
| 3.50 | Carnauba wax |
| 2.70 | Cyclomethicone/dimethiconol |
| 0.30 | Example 26 |
| 0.40 | Hydrogenated polyisobutene/cyclomethicone Phytantriol |
| 0.60 | Polyglycery-3 distearate/polysorbate 60/myristic acid/ {almitic acid/guar hydroxypropyltrimonium chloride/ *triticum vulgare* (wheat) flour lipids/avocado oil |
| QS 100 | Water |

The composition was prepared by combining the water soluble pigments and water phase and mixing well. The remaining oil phase ingredients were separately mixed. Both phases were combined and emulsified to form the final composition, which was a eyelash color in a rich black shade.

Formulation Example 2

A lipstick composition was prepared according to the following formula:

| w/w % | Material |
|---|---|
| 15.20 | Example 36 |
| 18.40 | Isostearyl alcohol |

-continued

| w/w % | Materal |
|---|---|
| 44.70 | Isododecane |
| 13.70 | Trioctyldodecyl citrate |
| 8.00 | Pigments and mica |

The composition was prepared by combining the ingredients with heat and mixing well.

Formulation Example 3

A long wearing foundation makeup composition in the emulsion form was prepared as follows:

| w/w % | Materal |
|---|---|
| 19.50 | Cyclomethicone/dimethicone copolyol |
| 0.50 | Sorbitan sesquioleate |
| 0.10 | Propyl paraben |
| 8.00 | Titanium dioxide/methicone |
| 0.10 | Silk powder |
| 1.21 | Mica/methicone |
| 1.00 | Iron oxides/methicone/boron nitride |
| 1.29 | Iron oxides/methicone |
| 2.00 | Nylon-12 |
| 3.50 | Boron nitride |
| 1.00 | Dimethicone |
| 5.00 | Trimethylsiloxysilicate |
| 9.00 | Cyclomethicone |
| 0.25 | lauryl dimethicone copolyol |
| 0.05 | Bisabolol |
| 1.50 | Tribehenin |
| 0.50 | Nylon-611/dimethicone copolymer/PPG-3 myristyl ether Glyceryl rosinate in isododecane (44:56) |
| 4.50 | Example 26 |
| 1.00 | Sodium chloride |
| 0.01 | Tetrasodium EDTA |
| 4.50 | Butylene glycol |
| 0.20 | Methylparaben |
| 3.00 | SD-alcohol 40B |
| 0.35 | Ethylene brassylate |
| 0.10 | Tocopheryl acetate |
| 0.05 | Retinyl palmitate |
| Qs to 100 | Water |

The composition was prepared by combining the water phase ingredients. Separately the oil phase ingredients were combined. The two phases were combined and mixed well to emulsify. The resulting foundation makeup was poured into bottles.

Formulation Example 4

A lip gloss composition is made as follows:

| w/w % | Materal |
|---|---|
| 4.00 | Triisostearyl citrate |
| 22.20 | Diiosostearyl malate |
| 7.40 | Octyldodecanol |
| 8.10 | Trioctyldodecyl citrate |
| 1.50 | Phenyl trimethicone |
| 6.20 | Polysilicone-6 |
| 12.30 | Example 32 |
| 2.50 | cyclomethicone |
| 0.40 | Methylparaben |
| 0.20 | Propyl paraben |

-continued

| w/w % | Materal |
|---|---|
| 0.10 | BHT |
| 0.20 | Benzoic acid |
| 6 20 | Isododecane |
| 12.30 | Polybutene |
| 7.10 | Mica/titanium dioxide |
| 1.40 | Mica/iron oxides/titanium dioxide |
| 4.80 | Mica |
| 4.30 | Pigments |

The composition is prepared by combining the ingredients with heat and mixing well. The resulting composition is a colored semi-solid.

Formulation Example 5

A face cream in the water and oil emulsion form is prepared as follows:

| w/w % | Materal |
|---|---|
| 5.00 | Glycerin |
| 5.00 | Xanthan gum |
| 0.30 | Trisodium EDTA |
| 0.05 | *Aloe Barbadensis* leaf juice |
| 0.50 | Methylparaben |
| 0.25 | Butylene glycol |
| 1.00 | Magnesium aluminum silicate |
| 1.00 | Magnesium ascorbyl phosphate |
| 0.20 | Phenyl trimethicone |
| 3.00 | Tocopheryl acetate |
| 1.00 | Butylene glycol dicaprylate/dicaprate |
| 9.00 | Dimethicone 350 cst viscosisty |
| 1.00 | C12-15 alkyl benzoate |
| 5.00 | Propylparaben |
| 0.10 | Phenoxyethanol |
| 1.00 | Cetyl alcohol |
| 4.00 | Example 35 |
| 2.00 | polyisobutene cyclomethicone Tetrahexyldecyl ascorbate |
| 1.00 | Glyceryl stearate/stearic acid/cetearyl |
| 5.00 | alcohol/palmitoyl hydrolyzed wheat protein |
| Qs to 100 | Water |

The composition is prepared by combining the oil phase and water phase ingredients separately, then mixing well to emulsify. The composition is of a creamy consistency.

Formulation Example 6

A sunscreen composition is prepared as follows:

| w/w % | Materal |
|---|---|
| 6.00 | Glycerin |
| 5.00 | Xanthan gum |
| 0.30 | Trisodium EDTA |
| 0.05 | *Aloe Barbadensis* leaf juice |
| 0.50 | Methylparaben |
| 0.25 | Butylene glycol |
| 1.00 | Magnesium aluminum silicate |
| 1.00 | Magnesium ascorbyl phosphate |
| 0.20 | Phenyl trimethicone |
| 3.00 | Tocopheryl acetate |
| 1.00 | Butylene glycol dicaprylate/dicaprate |
| 9.00 | Dimethicone 350 cps visxosity |
| 1.00 | C12-15 alkyl benzoate |
| 0.50 | Propylparaben |
| 0.10 | Phenoxyethanol |

-continued

| w/w % | Material |
|---|---|
| 1.00 | Cetyl alcohol |
| 4.00 | Example 35 |
| 2.00 | polyisobutene cyclomethicone |
| 2.00 | Oxybenzone |
| 7.50 | Octinoxate |
| 1.00 | Tetrahexyldecyl palmitate |
| 5.00 | Glyceryl stearate/stearic acid/cetearyl |
| QS 100 | Water |

The sunscreen composition is prepared by combining the oil phase and water phase ingredients separately, then combining and mixing well to emulsify.

Formulation Example 7

A liquid composition suitable for use as eyeliner was made as follows:

| w/w % | Material |
|---|---|
| 7.00 | Isododecane |
| 19.60 | Nylon 611/dimethicone copolymer/ |
| 5.00 | PPG-3 myristyl ether Polysilicone-6 |
| 25.00 | Blue 1 lake |
| 4.00 | Red 40 lake |
| 3.60 | Yellow 5 lake |
| 0.80 | Green 5 |
| 0.05 | Silica |
| 7.00 | Isododecane/quaternium-18 hectorite |
| 25.80 | propylene carbonate Dibutyl adipate |
| 2.95 | Methylparaben |
| 0.35 | Dehydroacetic acid |
| 0.20 | Propyl paraben |
| 0.10 | Sorbic acid |
| 0.06 | Example 36 |
| 5.50 | isododecane |

Formulation Example 8

A makeup remover composition was prepared as follows:

| w/w % | Material |
|---|---|
| 8.00 | Butylene glycol dicaprylate/dicaprate |
| 10.00 | Example 25 |
| 5.00 | Phenoxyethanol |
| 1.00 | Propylparaben |
| 0.10 | Isododecane/quaternium-18 hectorite/ |
| 20.00 | propylene carbonate Cetyl dimethicone copolyol |
| 2.50 | Cyclomethicone |
| 5.00 | Butylene glycol |
| 0.01 | Trisodium EDTA |
| 0.25 | Methylparaben |
| QS 100 | Water |

The composition is prepared by separately combining the oil phase ingredients and the water phase ingredients, then mixing well to emulsify.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A cosmetic composition comprising at least one silicone conforming to the following structure;

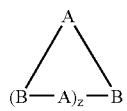

wherein;

A is

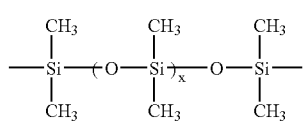

B is:

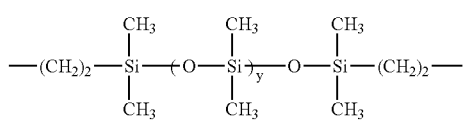

x is an integer ranging from 0 to 5000;

y is an integer ranging from 0 to 5000;

z is integer ranging from 2 to 2000, in which said composition is anhydrous or an emulsion.

2. The composition of claim 1 which is a water-in-oil emulsion or an oil-in-water emulsion.

3. The composition of claim 1 which is anhydrous.

4. The composition of claim 1 further comprising at least one oil.

5. The composition of claim 4 wherein the at least one oil is volatile.

6. The composition of claim 5 wherein the at least one volatile oil is a silicone, a hydrocarbon, or mixtures thereof.

7. The composition of claim 6 comprising about 0.1-95% by weight of the total composition of one or more volatile components.

8. The composition of claim 1 further comprising at least one additional film forming polymer.

9. The composition of claim 8 wherein the at least one additional film forming polymer is a non-silicone polymer.

10. The composition of claim 9 wherein the non-silicone polymer is a polymer comprised of polymerized ethylenically unsaturated monomers either alone or in combination with one or more organic moieties.

11. The composition of claim 1 further comprising a plasticizer in an amount sufficient to improve spreadability and application of the composition to the desired surface.

12. The composition of claim 11 wherein the plasticizer is present at about 0.01-60% by weight of the total composition.

13. The composition of claim 12 wherein the plasticizer is a glycerol, glycol, or citrate ester; or an ester of adipic or malic acid.

14. The composition of claim 1 further comprising one or more viscosity modifiers.

15. The composition of claim 14 wherein the viscosity modifying agent is present at 0.01-60% by weight of the total composition.

16. The composition of claim 15 wherein the viscosity modifying agent is selected from the group consisting of natural or synthetic montmorillonite minerals, associative thickeners, silicas, or silicate; or waxes.

* * * * *